US 8,855,752 B2

(12) United States Patent
Johnson (10) Patent No.: US 8,855,752 B2
(45) Date of Patent: Oct. 7, 2014

(54) QRS ONSET AND OFFSET DETECTION WITH ADAPTIVE TEMPORAL WINDOWING

(75) Inventor: Steven R. Johnson, Fair Haven, NJ (US)

(73) Assignee: Angel Medical Systems, Inc., Fair Haven, NJ (US)

( * ) Notice: Subject to any disclaimer, the term of this patent is extended or adjusted under 35 U.S.C. 154(b) by 1246 days.

(21) Appl. No.: 12/721,836

(22) Filed: Mar. 11, 2010

(65) Prior Publication Data

US 2011/0196246 A1  Aug. 11, 2011

Related U.S. Application Data

(63) Continuation-in-part of application No. 12/702,777, filed on Feb. 9, 2010, now Pat. No. 8,560,055.

(51) Int. Cl.
*A61B 5/0472* (2006.01)
(52) U.S. Cl.
CPC .................................... *A61B 5/0472* (2013.01)
USPC ............................ 600/509; 600/516; 600/517
(58) Field of Classification Search
CPC .. A61B 5/0402; A61B 5/0452; A61B 5/0472; A61B 5/7235; A61B 5/7239; A61B 5/7282
USPC .................. 600/508–509, 517, 521
See application file for complete search history.

(56) References Cited

U.S. PATENT DOCUMENTS

| | | | |
|---|---|---|---|
| 7,869,864 B2 * | 1/2011 | Tseng et al. | 600/517 |
| 2010/0241017 A1 * | 9/2010 | Johnson et al. | 600/509 |

* cited by examiner

*Primary Examiner* — Carl H Layno
*Assistant Examiner* — Jessica Anthony
(74) *Attorney, Agent, or Firm* — Rosenberg, Klein & Lee (57) ABSTRACT

A heart monitor computes ST segment deviation as the difference in the value of an electrocardiogram signal at the ST and PQ points of a heartbeat. The ST point is found based on slope criteria and temporal criteria. The maximum (positive) slope of the QRS (maxQRS) is located. Within a preset window after the maxQRS point, the processor searches for a sample at which the second finite difference is less than a threshold that is a function of average QRS amplitude. If such a qualifying sample is found, the processor examines its location relative to the location of an adaptive window that is centered on a sample that is an adaptively determined distance from the peak of the R wave. If the qualifying point is within the adaptive window, it is chosen as the ST point. If the qualifying point is after the adaptive window, the ST point is set at the end of the adaptive window. Finally, if the qualifying point is before the adaptive window, the ST point is selected at the beginning of the adaptive window. The adaptive window is then updated according to an exponential average filter based upon the distance between the ST point and the R wave peak.

12 Claims, 11 Drawing Sheets

SEGMENT BASED PROCESSING

QRS ONSET AND OFFSET DETECTION WITH ADAPTIVE TEMPORAL WINDOWING

CROSS REFERENCE TO RELATED APPLICATIONS

This application claims priority to U.S. patent application Ser. No. 12/702,777, filed 9 Feb. 2010, entitled "SYSTEM AND METHODS FOR THE SELECTIVE UPDATING OF HEART SIGNAL PARAMETER TIME SERIES."

FIELD OF USE

This invention is in the field of medical device systems that monitor a patient's cardiovascular condition.

BACKGROUND OF THE INVENTION

Heart disease is the leading cause of death in the United States. A heart attack, also known as an acute myocardial infarction (AMI), typically results from a blood clot or "thrombus" that obstructs blood flow in one or more coronary arteries. AMI is a common and life-threatening complication of coronary artery disease. Coronary ischemia is caused by an insufficiency of oxygen to the heart muscle. Ischemia is typically provoked by physical activity or other causes of increased heart rate when one or more of the coronary arteries is narrowed by atherosclerosis. AMI, which is typically the result of a completely blocked coronary artery, is the most extreme form of ischemia. Patients will often (but not always) become aware of chest discomfort, known as "angina", when the heart muscle is experiencing ischemia. Those with coronary atherosclerosis are at higher risk for AMI if the plaque becomes further obstructed by thrombus.

Detection of AMI often involves analyzing changes in a person's ST segment voltage. A common scheme for computing changes in the ST segment involves determining a quantity known as ST deviation for each beat. ST deviation is the value of the electrocardiogram at a point or points during the ST segment relative to the value of the electrocardiogram at some point or points during the PQ segment. A variety of schemes have been proposed to automatically determine both ST points and PQ points.

U.S. Pat. No. 6,397,100 discloses a method for detecting the isoelectric point (PQ point) for the QRST complex, by searching backwards from the R wave peak for a locally minimum slope.

Hayn et al., ("Automated QT Interval Measurement from Multilead ECG Signals", Comp. Card. 33:381-4, 2006) describe a method for detecting Q wave onset by first selecting a coarse QRS onset point by comparing the change in the signal over time (i.e. gradient) to a threshold. This coarse onset point is then fine tuned by a stepwise decrease of the threshold. For each such step, a "possible onset point was calculated and the mean range curve value right before and after this possible point was determined. The point with the lowest ratio in between these mean values was chosen as the exact onset point." The "range curve" is the difference in signal amplitude, so a ratio of range curves before and after a point is a ratio of first derivative/gradient quantities.

Sun et al. ("Characteristic wave detection in ECG signal using morphological transform"; BMC Cardiovasc Disord. 2005; 5: 28) describe a multi-scale derivative method for locating QRS (and P and T) wave fiducial points. "Long distance" derivatives/differences (e.g. f(x+n)−f(x), where n>1) are taken both before and after each candidate onset point and the difference between these derivatives is calculated to form a type of second derivative/difference which the authors term a "multiscale morphological derivative transform." QRS onset or other fiducial points are defined as the maxima or minima of this "transform." Kemmelings et. al. describe a QRS onset/offset detection scheme that involves summing the absolute value of the first derivative (difference) and then taking a "long distance" derivative of this summed signal, to find where it abruptly changes (over a large scale). ("Automatic QRS onset and offset detection for body surface Q RS integral mapping of ventricular tachycardia."; IEEE Trans Biomed Eng. 1994; 41:830-836).

Zong et al. ("A robust open-source algorithm to detect onset and duration of QRS complexes", Computers in Cardiology, 2003, Issue, 21-24 Sep. 2003, Page(s): 737-740) describe a method for detecting QRS onset and offset points by applying thresholds to the values of a function that corresponds to the "distance" along the signal; the function has the form $(D^2+(\Delta s/\Delta t)^2)^{0.5}$, where D is a constant and $\Delta s$ is the difference between successive samples of an ECG signal and $\Delta t$ is the time between samples (i.e. the inverse of the sampling frequency). This function is essentially a discrete version of the calculus formula for distance along a curve, which is based on the first derivative of the curve.

U.S. Pat. No. 5,758,654 describes a method for QRS onset/offset detection. First, a QRS peak is located based upon, among other things, second derivative criteria. Adjacent QRS extrema (i.e. peaks) are located, apparently by stepping through consecutive waveform samples, and selected as coarse QRS onset/offset times. The coarse onset/offset times are subsequently refined based on criteria related to the region of the waveform bounded by optimal QRS onset/offset points.

U.S. Pat. No. 6,650,931 to McClure et al. describes search techniques for finding the onsets and offsets of various cardiac events. To detect QRS offset points, a search is performed within a predefined search window. One criterion for a valid QRS offset point is that "the absolute value of the summation of the differences between a given number of consecutive pairs of sample points occurring .$\Delta t$ msec apart" must be less than a pre-defined value. Also, "the maximum amplitude of all the signal sample points used in satisfying [the above criterion] must be less than a pre-defined maximum amplitude."

U.S. Pat. No. 6,625,490 to McClure et al. describes a "System and method of automatically adjusting sensing parameters based on temporal measurement of cardiac events."

Laguna et al. (Automatic detection of wave boundaries in multilead ECG signals: validation with the CSE database Source Computers and Biomedical Research, Volume 27, Issue 1 (February 1994), describe a method for detecting QRS offset by applying a slope test. The QRS maximum is located, and the ST point is chosen as the point after that at which the slope decreases to a specified fraction of the maximum slope. If no such sample is found, then the minimum value of the slope is taken as the ST point.

Despite all of the foregoing work that has been done, there is still a need for an effective system for detecting QRS onset and offset points.

SUMMARY OF THE INVENTION

An embodiment of the present invention comprises a heart monitor that may be chronically implanted or external. The device, which includes an analog to digital convertor and a processor that performs beat detection, monitors the time course of a heart signal parameter, namely ST segment deviation, computed from an electrocardiogram. An ST deviation time series is generated by a recursive filter that is preferably an exponential average filter whose output is a weighted sum of the then existing ST time series value and current ST deviation values of analyzable beats.

ST deviation is the difference between ST and PQ points. The ST point is found by performing the following steps. First, the processor locates the maximum (positive) slope of the QRS (maxQRS). Within a preset window after the maxQRS point, the processor searches for a sample at which the second finite difference is less than a threshold that is a function of average QRS amplitude. If such a qualifying sample is found, the processor examines its location relative to the location of an adaptive window that is centered on a sample that is an adaptively determined distance from the peak of the R wave.

If the qualifying point is within the adaptive window, it is chosen as the ST point. If the qualifying point is after the adaptive window, the ST point is set at the end of the adaptive window. Finally, if the qualifying point is before the adaptive window, the ST point is selected at the beginning of the adaptive window. The adaptive window is then updated according to an exponential average filter based upon the distance between the ST point and the R wave peak.

DETAILED DESCRIPTION OF THE INVENTION

Architecture

Figure 1:
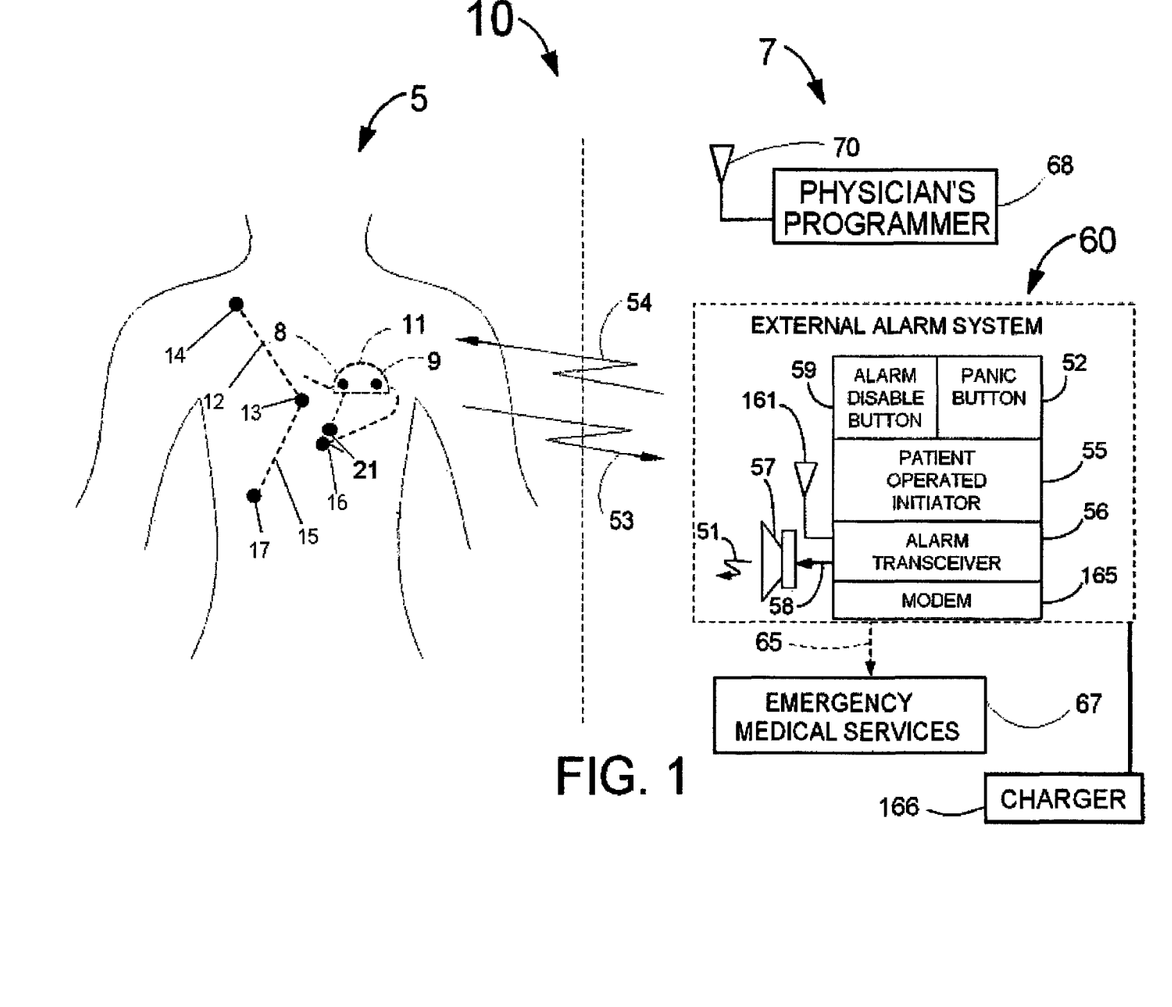
FIG. 1 illustrates a system for the detection of a cardiac event and for warning the patient that a medically relevant cardiac event is occurring.

FIG. 1 illustrates one embodiment of a system 10 comprising an implanted cardiac event detection device 5 and external equipment 7. The battery powered cardiac diagnostic device 5 contains electronic circuitry that can detect a cardiac event such as an acute myocardial infarction or arrhythmia and warn the patient when the event, or a clinically relevant precursor, occurs. The cardiac diagnostic device 5 can store the patient's electrocardiogram for later readout and can send wireless signals 53 to and receive wireless signals 54 from the external equipment 7. The functioning of the cardiac diagnostic device 5 will be explained in greater detail with the assistance of FIG. 2.

The cardiac diagnostic device 5 receives electrical signals from intracardiac, subcutaneous or body surface leads 12 and 15, which in the embodiment illustrated here will be a clavicle and right side lead, respectively. Clavicle lead 12 comprises electrodes 13 and 14 with polarity hereafter defined as the difference potential measured between electrode 13 and electrode 14. Right side lead 15 comprises electrodes 13 and 6 with polarity hereafter defined as the potential at electrode 13 minus the potential at electrode 6. The electrode 13 is preferably disposed as close as possible to the sternum, in the fourth intercostal space on the right side of the body. The electrode 6 may be positioned to reduce ST deviation changes associated with heart rate changes by aligning the lead parallel to ST segment deviation contours. (See Hopenfeld B., "ST segment depression: the possible role of global repolarization dynamics", Biomed Eng Online. 2007 Feb. 9; 6:6). The electrode position may be selected by, for example, performing a stress test with electrodes in a few different positions inferior and to the right of electrode 13 (while maintaining a minimum distance from electrode 13).

The clavicle lead 12 measures the electrical signal between the upper right clavicle and a medial region over the area of the sternum and is therefore generally less than 15 cm long; the clavicle lead 12 is approximately aligned with the long axis of the heart. The right side lead 15 measures the electrical signal between the right precordial chest region and an inferior right lateral or posterior torso position. The cardiac diagnostic device 5 is housed in a metal case 11 that can serve as another electrode. The cardiac device 5 is shown in the left upper pectoral region but may be implanted in any convenient location such as the upper right pectoral region.

Many other embodiments of the present invention are possible. In one alternative embodiment, a lead is implanted within the heart, and the detection method of the present invention may be applied to signals received through that lead. In another alternative embodiment, subcutaneous electrodes in the following areas are used to form three separate leads: (1) the left precordial area (12 lead ECG lead V2); (2) the upper left pectoral region; and (3) the lowest portion on the left ribcage on the midaxillary line.

Also, as will be described more fully below, the present invention may be used in conjunction with an implantable cardioverter/defibrillator, a pacemaker or biventricular pacemakers (cardiac resynchronization therapy devices), or different types of implantable monitors (such as an implantable ventricular chamber pressure sensor or temperature sensor). In this case, an intracardiac lead 21, for example in the RV apex with the housing 11 serving as a reference potential, may provide electrical signals for analysis. Extracardiac leads could also be employed.

If the portable detection device described herein is used in conjunction with any of the above mentioned therapeutic devices, according to one embodiment of the present invention, alarm data (associated with the present invention's detection scheme) is sent from the device through a service such as St. Jude Merlin.net or Medtronic Carelink. The service, in turn, notifies the patient that he/she needs to seek treatment. According to a possible implementation of this embodiment, the portable detection device does not require an internal alarm, thereby decreasing the size of the portable device.

FIG. 1 also shows the external equipment 7 that consists of a physician's programmer 68 having an antenna 70, an external alarm system 60 including a charger 56. The external equipment 7 provides means to interact with the cardiac diagnostic device 5. These interactions include programming the cardiac diagnostic device 5, retrieving data collected by the cardiac diagnostic device 5 and handling alarms generated by the cardiac diagnostic device 5. The operation of these components is further described in U.S. patent application publication number 2004/0215092.

Figure 2:
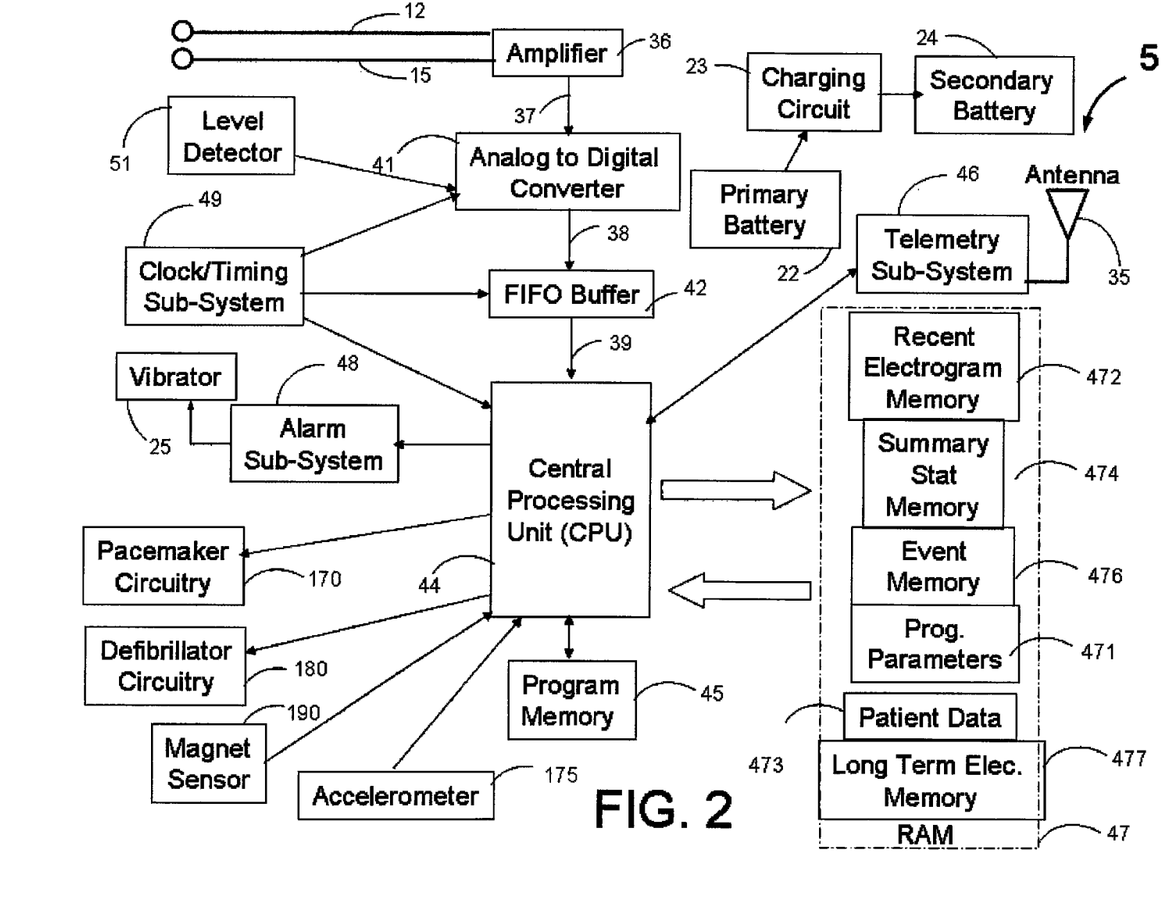
FIG. 2 is a block diagram of an implanted cardiac diagnostic system according to the present invention.

FIG. 2 is a block diagram of the cardiac diagnostic device 5 with primary battery 22 and a secondary battery 24. The secondary battery 24 is typically a rechargeable battery of smaller capacity but higher current or voltage output than the primary battery 22 and is used for short term high output components of the cardiac diagnostic device 5 like the RF chipset in the telemetry sub-system 46 or the vibrator 25 attached to the alarm sub-system 48. According to a dual battery configuration, the primary battery 22 will charge the secondary battery 24 through the charging circuit 23. The primary battery 22 is typically a larger capacity battery than the secondary battery 24. The primary battery also typically has a lower self discharge rate as a percentage of its capacity than the secondary battery 24. It is also envisioned that the secondary battery could be charged from an external induction coil by the patient or by the doctor during a periodic check-up.

The pairs of wires corresponding to leads 12 and 15 respectively connect to the amplifier 36, which is a multi-channel or differential amplifier. The amplified electrocardiogram signals 37 from the amplifier 36 are then converted to digital signals 38 by the analog-to-digital converter 41, which preferably samples at a rate of at least 200 Hz. The temporal resolution of the sampling is relevant with regard to the sampling of the high frequency components of a heartbeat's activation (QRS) complex. The digital electrocardiogram signals 38 are buffered in the First-In-First-Out (FIFO) memory 42. Processor means shown in FIG. 2 as the central processing unit (CPU) 44 coupled to memory means shown in FIG. 2 as the Random Access Memory (RAM) 47 can process the digital electrocardiogram data 38 stored the FIFO 42 according to the programming instructions stored in the program memory 45 that implement the flowcharts shown in FIGS. 3-6. This programming (i.e. software) enables the cardiac diagnostic device 5 to detect the occurrence of a cardiac event such as an acute myocardial infarction.

Figure 6A:
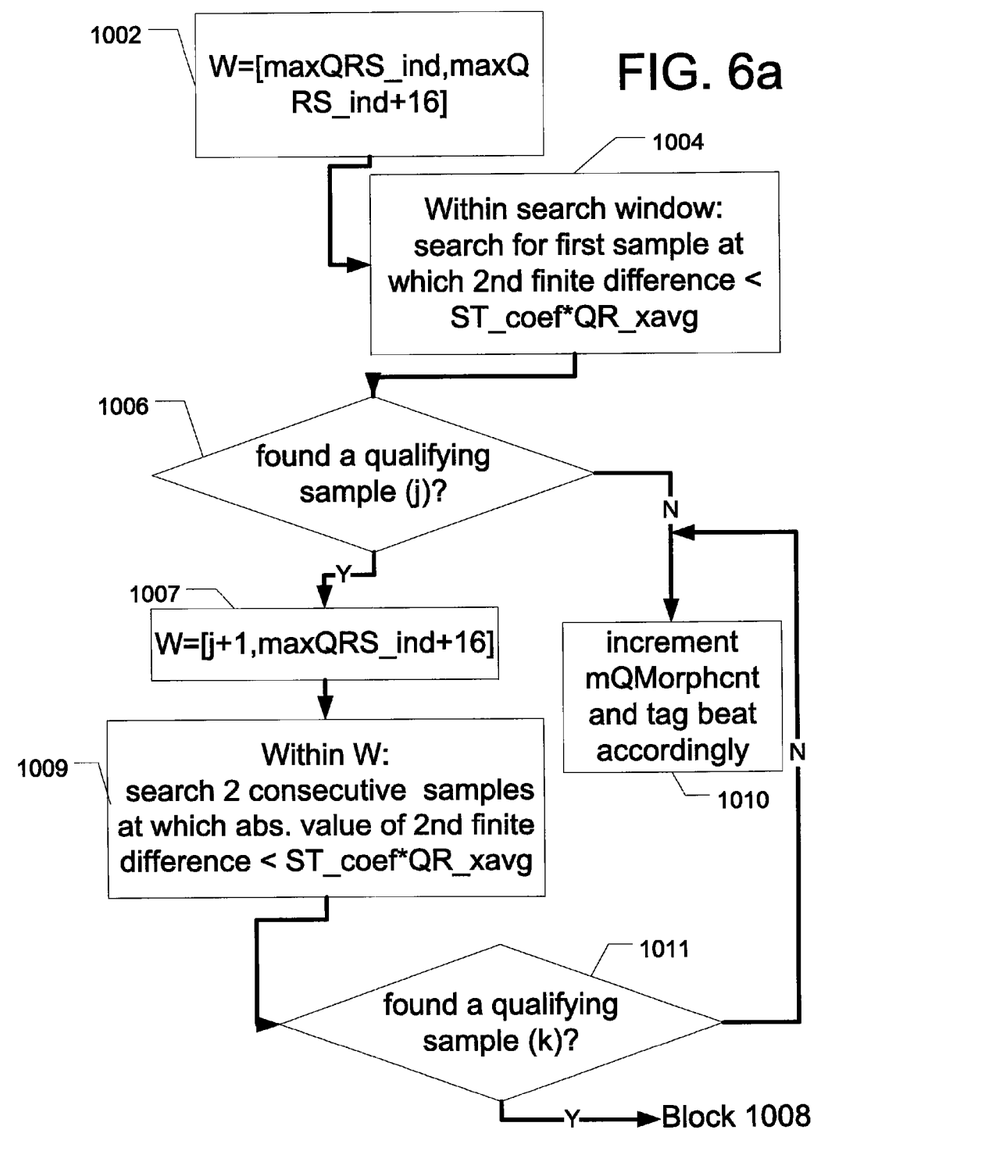
FIGS. 6a and 6b are a flow chart of the preferred embodiment for determining the location of PQ and ST points.
Figure 6B:
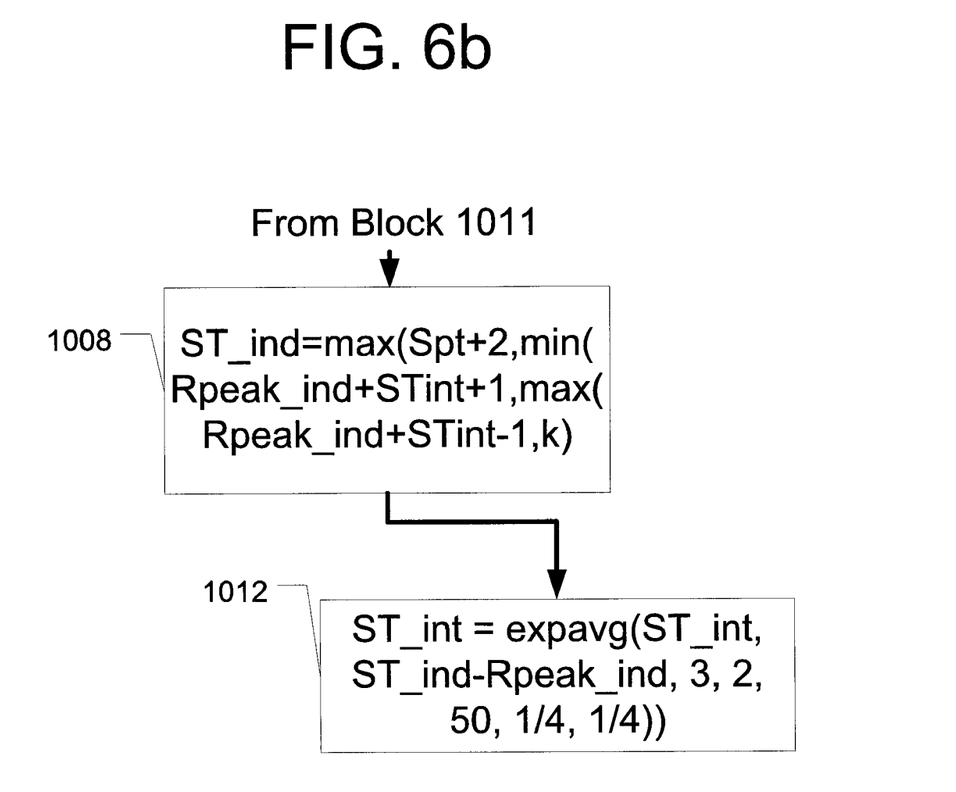

An acute myocardial infarction is detected by analyzing a person's ST segment deviation, which is the difference between ST and PQ points within the electrical manifestation of a heartbeat. The routine described with reference to FIG. 6 shows a preferred scheme for locating ST points.

A level detector 51 is coupled to the analog to digital converter 41. The level detector 51 detects whether a patient's torso is upright or supine and also, if the torso is supine, the extent of its rotation with respect to the earth (e.g. patient is lying flat on his/her back, lying on his/her right side or left side.) Many MEMS based level detects which can also operationally serve as inclinometers, accelerometers, and general detectors for motion/force exist.

Additional sensors may communicate with the device 5 wirelessly through the telemetry sub-system. The data from these leads may correspond to digitized electrocardiogram signals (that have been processed by a remote subcutaneous device).

The operation of most of the components in FIG. 2 is further described in U.S. patent application publication number 2004/0215092.

In a preferred embodiment of the present invention the RAM 47 includes specific memory locations for 4 sets of electrocardiogram segment storage. These memory locations are the recent electrocardiogram storage 472 that would store the last 2 to 10 minutes of recently recorded electrocardiogram segments so that the electrocardiogram data occurring just before the onset of a cardiac event can be reviewed at a later time by the patient's physician using the physician's programmer 68 of FIG. 1. For example, the recent electrocardiogram storage 472 might contain eight 10-second long electrocardiogram segments that were captured every 30 seconds over the last 4 minutes.

A summary statistics memory 474 would provide storage for summary information, such as running averages, of various cardiac waveform feature values. A long term electrocardiogram memory 477 would provide storage for electrocardiograms collected over a relatively long period of time. In the preferred embodiment, every ninth electrocardiogram segment that is acquired is stored in a circular buffer, so that the oldest electrocardiogram segments are overwritten by the newest one.

The telemetry sub-system 46 with antenna 35 provides the cardiac diagnostic device 5 the means for two-way wireless communication to and from the external equipment 7 of FIG. 1. Existing radiofrequency transceiver chip sets such as the Ash transceiver hybrids produced by RF Microdevices, Inc. can readily provide such two-way wireless communication over a range of up to 10 meters from the patient. It is also envisioned that short range telemetry such as that typically used in pacemakers and defibrillators could also be applied to the cardiac diagnostic device 5. It is also envisioned that standard wireless protocols such as Bluetooth and 802.11a or 802.11b might be used to allow communication with a wider group of peripheral devices.

Flowcharts

FIGS. 3a-3d, along with FIGS. 6a and 6b, are collectively a flow chart of a routine that finds the location of the samples that are used to determine ST deviation. Roughly, ST deviation is a function of the difference in signal amplitude between the ST and PQ segments of a heart beat. The flowchart will be described with respect to one embodiment for finding the location within a beat at which to measure PQ segment amplitude. Analogous steps may be performed to find an appropriate ST segment measurement point. However, the preferred embodiment for finding both PQ and ST segment measurement points will be described with reference to FIGS. 6a and 6b.

The flowcharts described below incorporate the following definitions: D[i] is the value at point/sample i within a segment; and S[i] is the slope at point i,=D[i+3]+2*D[i+2]+D[i+1]−D[i−1]−2*D[i−2]−D[i−3]. The exponential average of a variable (V) is expavg(V, $\Delta$, $\alpha$, min, max, mindelt, maxdelt), which means that the variable V is updated by the current value $\Delta$, with an update weighting $1/2^\alpha$, subject to constraints on the maximum and minimum allowable value for the variable and changes in that variable. Ignoring the constraints, expavg(V, $\Delta$, $\alpha$, [ ], [ ], [ ], [ ]) is $V(j+1)=((2^\alpha-1)*V(j)+\Delta)/2^\alpha$.

The method described in FIGS. 3a-3d determines PQ and ST points only for normal beats. Abnormal beats are detected and noted but their ST deviation is not computed. A normal beat for a particular lead is dependent on the orientation of that lead with respect to the heart and other patient specific factors. In the method described in FIGS. 3a-3d, a normal beat is assumed to have a significant downstroke, i.e. a normal beat does not include a QRS morphology characterized by a single large upstroke followed by a single large downstroke.

Blocks 800 through 822 (FIG. 3a, 3b, 3c) are performed iteratively for each beat in a segment of electrocardiogram data. Before the PQ/ST location diction is invoked, a segment of data has been analyzed to detect beats, preferably by a routine based on the slope based scheme described in U.S. patent application Ser. No. 12/232,281, entitled "Methods and Apparatus for Detecting Cardiac Events Based on Heart Rate Sensitive Parameters", filed September 2008, owned by the assignee of the present invention. For each beat, the absolute minimum of the QRS (Rpeak) is located and the location of the preceding positive peak (initpk), if any, is determined. The average RR interval for the segment is computed. Based on the average RR interval, PVC beats are located, tagged, and not included in the segment's ST deviation; the PQ and ST times are not located for PVC beats.

For each non-PVC beat in the segment, in block 800, the minimum QRS slope (minQRS) is located. Block 802 searches for a positive peak in the slope (maxQRS) within a search window located after Rpeak. In particular, the search window begins at 2 samples after Rpeak and ends 12 samples after Rpeak. In the figures, a search window is denoted by W[a,b], where a is the window starting point (sample index integer) and b is the window ending point. The sample index (location) associated with a particular reference point is denoted by appending "_ind" to the particular reference point. For example, the index associated with Rpeak is Rpeak_ind. The preferred window values, and all other time based values associated with FIGS. 3-6, are based on a 200 Hz sampling rate.

Figure 3A:
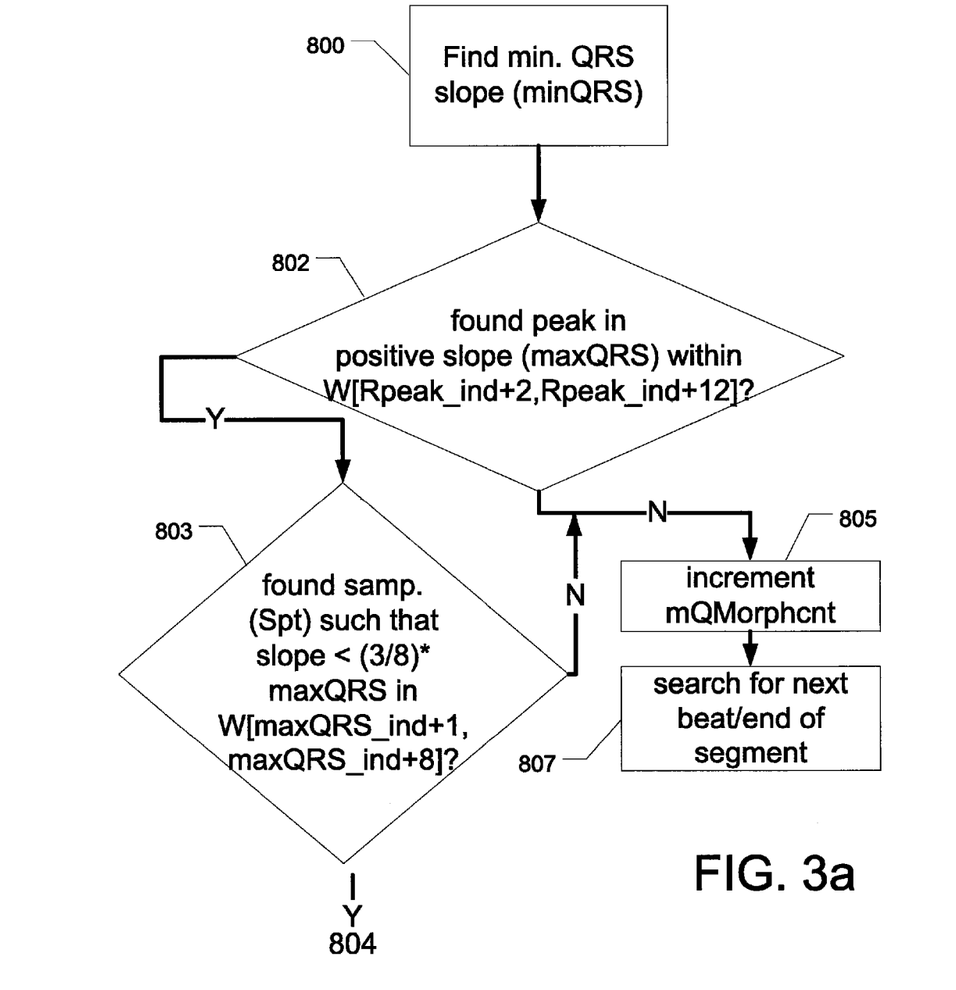
FIGS. 3a-3d are collectively a flow chart of a routine that processes electrocardiogram/electrocardiogram segments to perform morphology checking on QRS complexes and determines the location of PQ points for analyzable QRS complexes.

If a local peak in the positive slope is found at either end of the purposely too wide search window designated in block 802, block 805 increments the "bad beat counter" labeled as mQMorphcnt and in block 807 the routine searches for the next beat or the end of the segment. Otherwise, if block 802 has found a local positive slope peak, control transfers to block 803, which checks to see if there is an appropriate decrease in the positive slope after maxQRS. In particular, within W[maxQRS_ind+1, maxQRS_ind+8], the routine searches for the first point where the slope is less than ⅜ of maxQRS. If no such sample can be found, the beat is tagged as irregular, the mQRMorphcnt is incremented in block 805, and processing continues in block 807. Otherwise, control passes to block 804 in FIG. 3b.

In block 804 (FIG. 3b), the routine determines whether the beat has been classified (by the segment based QRS detection routine) as having an initial positive peak (initpk). If so, in block 806, the PQ search window is set at [initpk_ind−2, initpk_ind−5] so that it precedes the initial peak. Otherwise, in block 808, the initial search window is set at [minQRS_ind−6, minQRS_ind−20] so that it precedes minQRS.

Figure 3B:
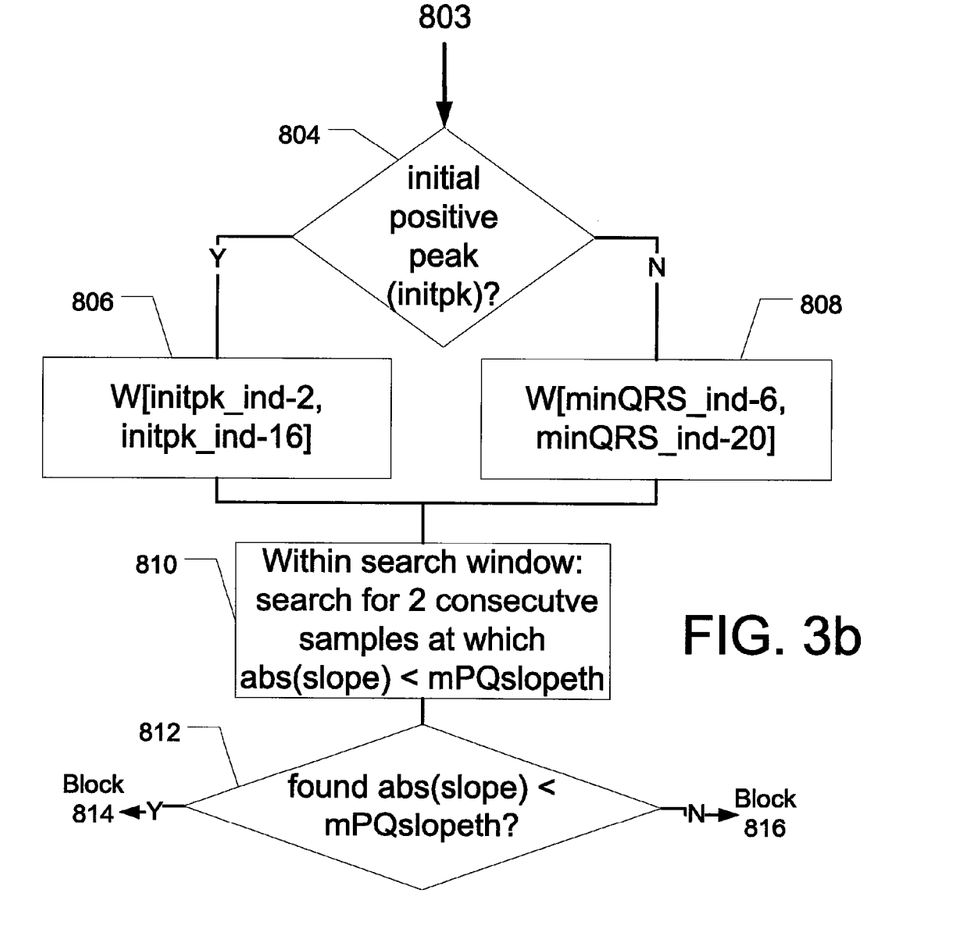

Control from either block 806 or block 808 passes to block 810, which searches for the first of two consecutive samples at which the absolute value of the slope is less than an adaptive threshold, mPQslopeth. The search is performed backwards, starting at the beginning of the search window. (More generally, if W[a,b] is such that a>b, the search in window W is performed backwards.) The slope is preferably an average of values at surrounding samples; in the preferred embodiment, S[i]=D[i+3]+2*D[i+2]+D[i+1]−D[i−1]−2*D[i−2]−D[i−3]. If two consecutive samples are found that satisfy the slope test, then block 812 passes control to block 814 (FIG. 3c), which sets the PQ point as the index of the first of the two consecutive samples.

Figure 3C:
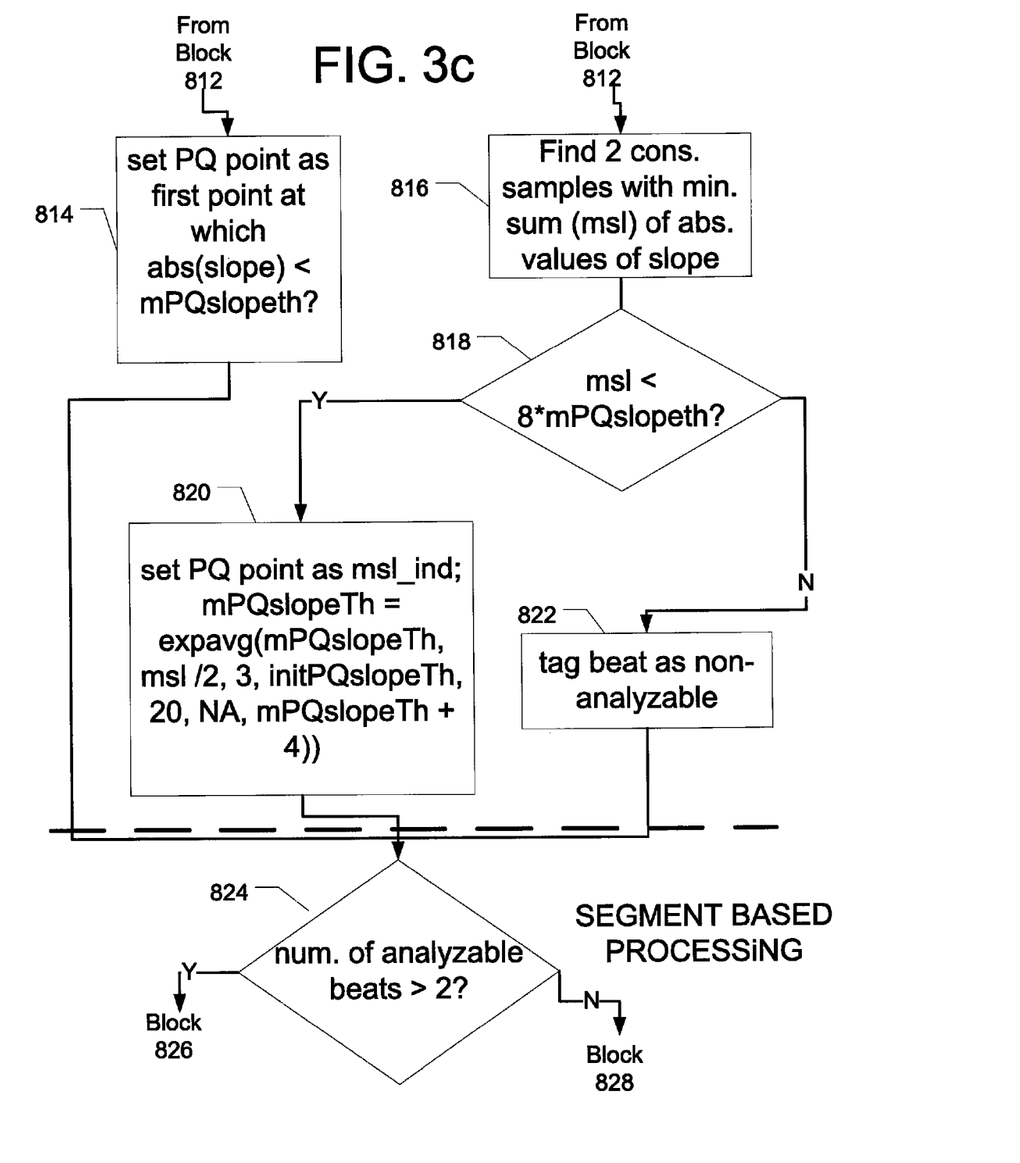

Returning to block 812 (FIG. 3b), if two consecutive samples that pass the test in block 810 are not found, then block 812 passes control to block 85 (FIG. 3c). Block 85 finds the two consecutive samples with the minimum sum (msl) of absolute values of slope within the search window. Block 85 transfers control to block 818, which checks whether msl is less than a maximum allowable threshold, preferably equal to 8 times (a factor of 2 because msl is a sum of 2 slopes and a factor of 4 to ensure the slope isn't wildly different from the norm) mPQslopeth. If msl is greater than the maximum allowable threshold, the beat is tagged as non-analyzable in block 822. An analyzable beat is one whose ST deviation is computed. In an alternate embodiment, the mQRMorphcnt is also incremented. Otherwise, if msl is less than the maximum allowable threshold, the PQ point is set at the first of the two points (msl_ind) and mPQslopeth is updated (increased) based on the value of msl.

After all the beats in a segment have been processed, segment based processing resumes in block 824, which checks whether the number of analyzable beats in the segment is greater than two. If so, control passes to block 826 (FIG. 3d), which computes the average PQ slope of the segment (PQslopeThavg) based on the slopes at the PQ points for each analyzable beat in the segment. If the number of analyzable beats in the segment is less than or equal to two, control passes to block 828 (FIG. 3d), which sets PQslopeThavg as the existing PQ slope threshold (mPQslopeTh). From either block 826 or 828, control passes to block 830 (FIG. 3d), which computes the outcome of a number of tests that are compounded in block 832 to determine whether to update mPQslopeTh. In particular, blocks 830 and 832 determine that an update should occur in block 834 if: (1) at least 3 beats in the segment are analyzable and either: (2) the average segment RR interval is between ¾ and 3/2 of the previous segment's average RR interval; or (3) mQMorphCnt is less than 2 and the number of PVC's in the segment is less than 2. As will be further described below, the number of analyzable beats is tracked by STDNcnt in block 858 of FIG. 4a. In an alternate embodiment, the determination whether to update exponential averages is based on a variable, mqmornh (see FIG. 5 and associated discussion) that tracks long term trends in the relative frequency of abnormal beats.

Figure 3D:
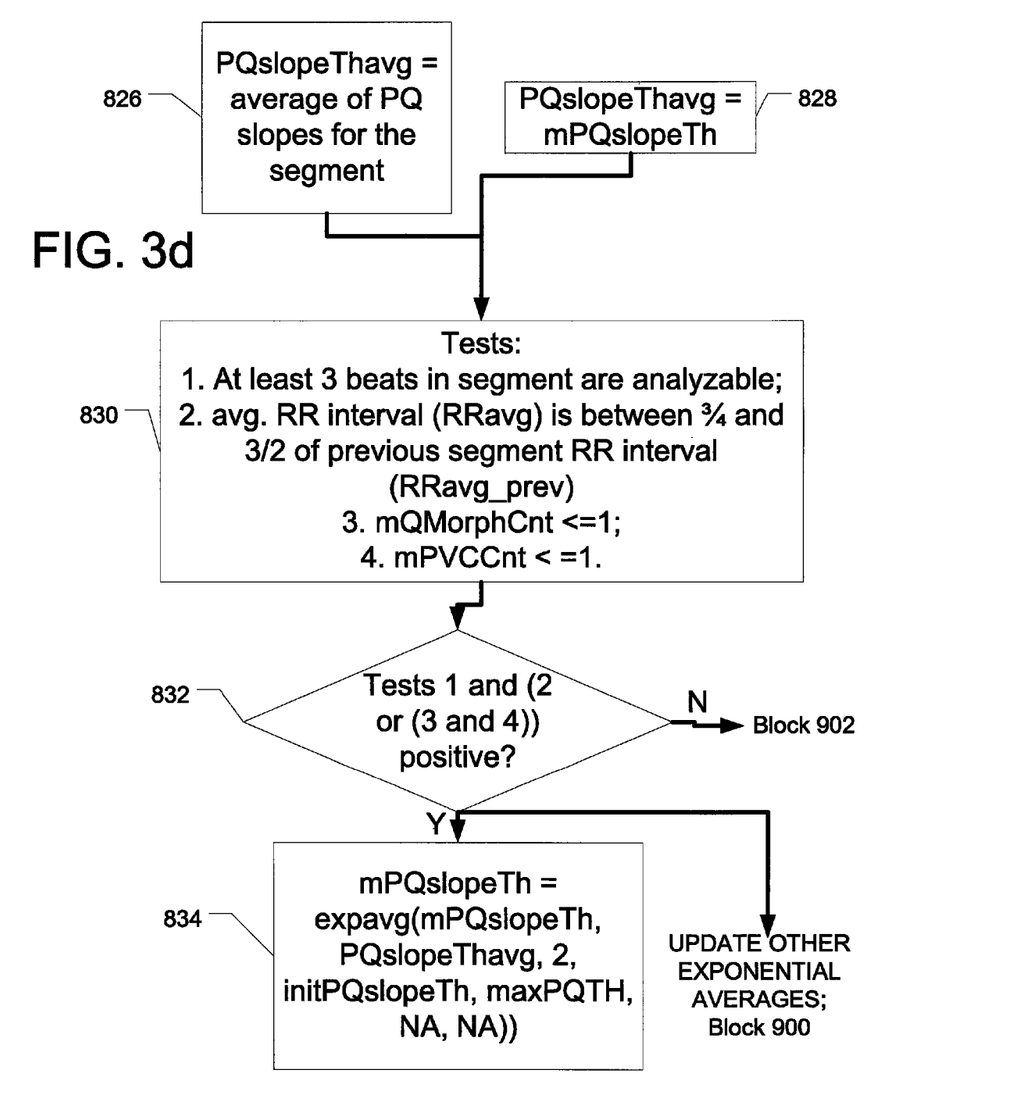

Block 834 updates mPQslopeTh by computing an exponential average based on PQslopeThavg. The updating is performed such that mPQslopeTh can never be less than initPQslopeTh, an empirically determined value, and can never be greater than an empirically determined value, maxPQTH. The initial mPQslopeTh is set at initPQslopeTh.

Figure 4A:
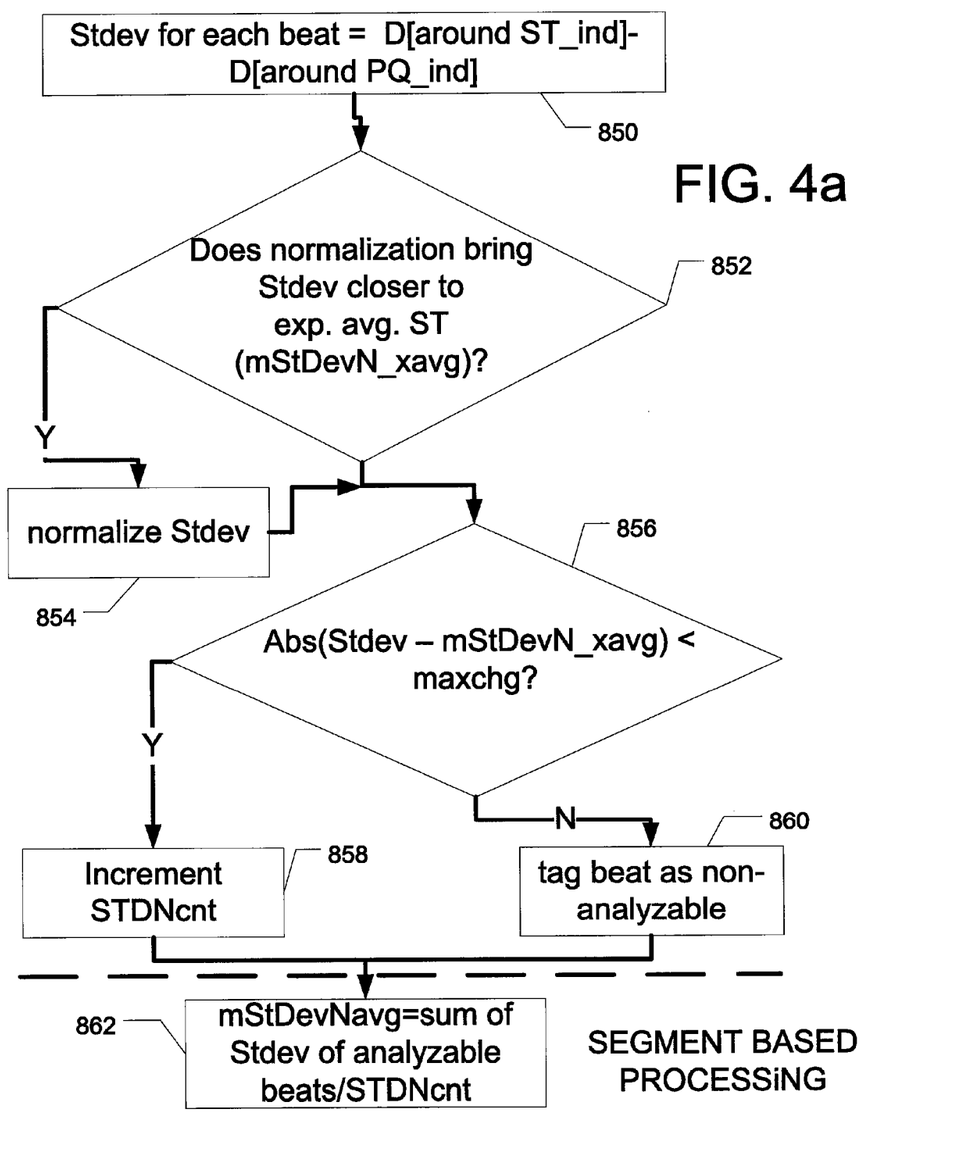
FIGS. 4a-4b are a flowchart that shows steps for determining a measure of segment based ST deviation and a long term exponential average filtered version of ST deviation.
Figure 4B:
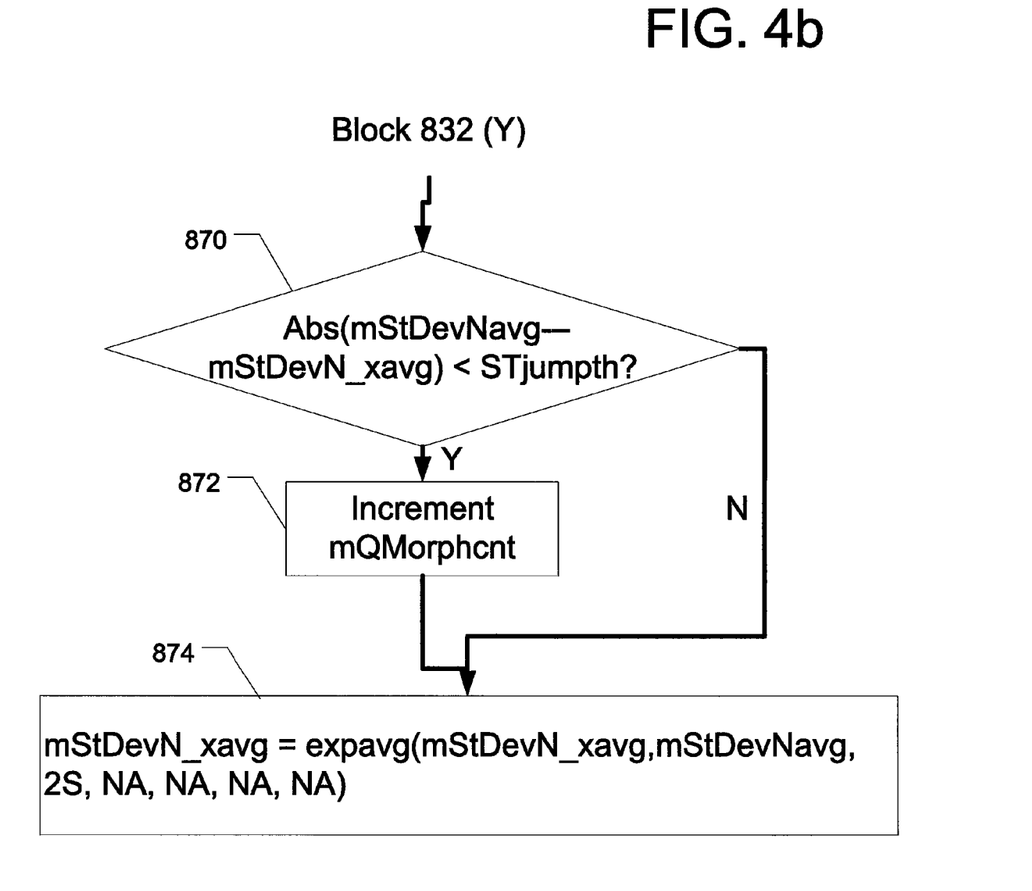

FIGS. 4a and 4b are a flow chart of the preferred method for computing effective ST segment deviation (mStDevN_xavg), which is an averaged, filtered version of a number of beat based ST deviation measurements. FIG. 4a shows steps that are performed for each (provisionally) analyzable beat that has associated ST and PQ points, preferably determined according to the methods described in FIGS. 3a-3d and FIGS. 6a and 6b, respectively. In block 850, ST deviation (Stdev) is determined by the difference between the signal values of the samples surrounding the ST and PQ points, respectively. In the preferred embodiment, the PQ signal value is equal to the average of the signal over four consecutive samples starting at the sample that is two samples earlier than the PQ point. In the preferred embodiment, the ST signal value is equal to the average of the signal over four consecutive samples starting at the sample that is one sample earlier than the ST point.

Block 852 determines whether a normalized Stdev is closer to the existing long term averaged ST deviation (mStDevN_xavg). Normalization may be important due to amplitude changes in the signal that can result from a shift in patient postures or other causes. More than one type of normalization may be tried. The following are a preferred list of normalization possibilities, where QR is QRS amplitude, the maximum peak to peak amplitude of the QRS, and QR_sh and QR_long are short and long term exponential averages of QR, respectively: (1) normalize by multiplying Stdev by (QR_long/QR_short); (2) normalize by dividing ST_dev by QR_short (or multiplying by a decreasing function of QR like 1−QR_sh); (3) normalize by dividing ST_dev by a non-linear function of QR that saturates at high and low values of QR (or multiplying by a function that is an inverse of the non-linear function).

In an alternative embodiment, block 852 determines whether a normalized Stdev is closer to the existing normal ST deviation at the given RR interval based on past history/histograms.

If normalization brings Stdev closer to then existing long term averaged ST deviation (mStDevN_xavg), then Stdev is normalized in block 854. Control passes to block 856, which checks whether the difference between Stdev and mStDevN_xavg exceeds a threshold. If so, the beat is tagged as non-analyzable in block 860 and does not figure into the segments average ST deviation. Otherwise, an analyzable ST deviation beat counter is incremented in block 858. The segment average ST deviation (mStDevNavg) is calculated in block 862.

Processing continues at block 870, shown in FIG. 4b if the test in block 832 (FIG. 3d) is satisfied. Block 870 checks whether the difference between mStDevNavg and the current long term, filtered ST time series (mStDevN_xavg) exceeds a threshold. If so, mQMorphcnt is incremented in block 872. Otherwise, control passes to block 874, which updates mStDevN_xavg based on mStDevNavg. The filtered change in mStDevNavg may also be computed based on the difference between the values of mStDevNavg before (old_mStDevN_xavg) and after (mStDevN_xavg) the above mentioned update of mStDevN_xavg.

Figure 5:
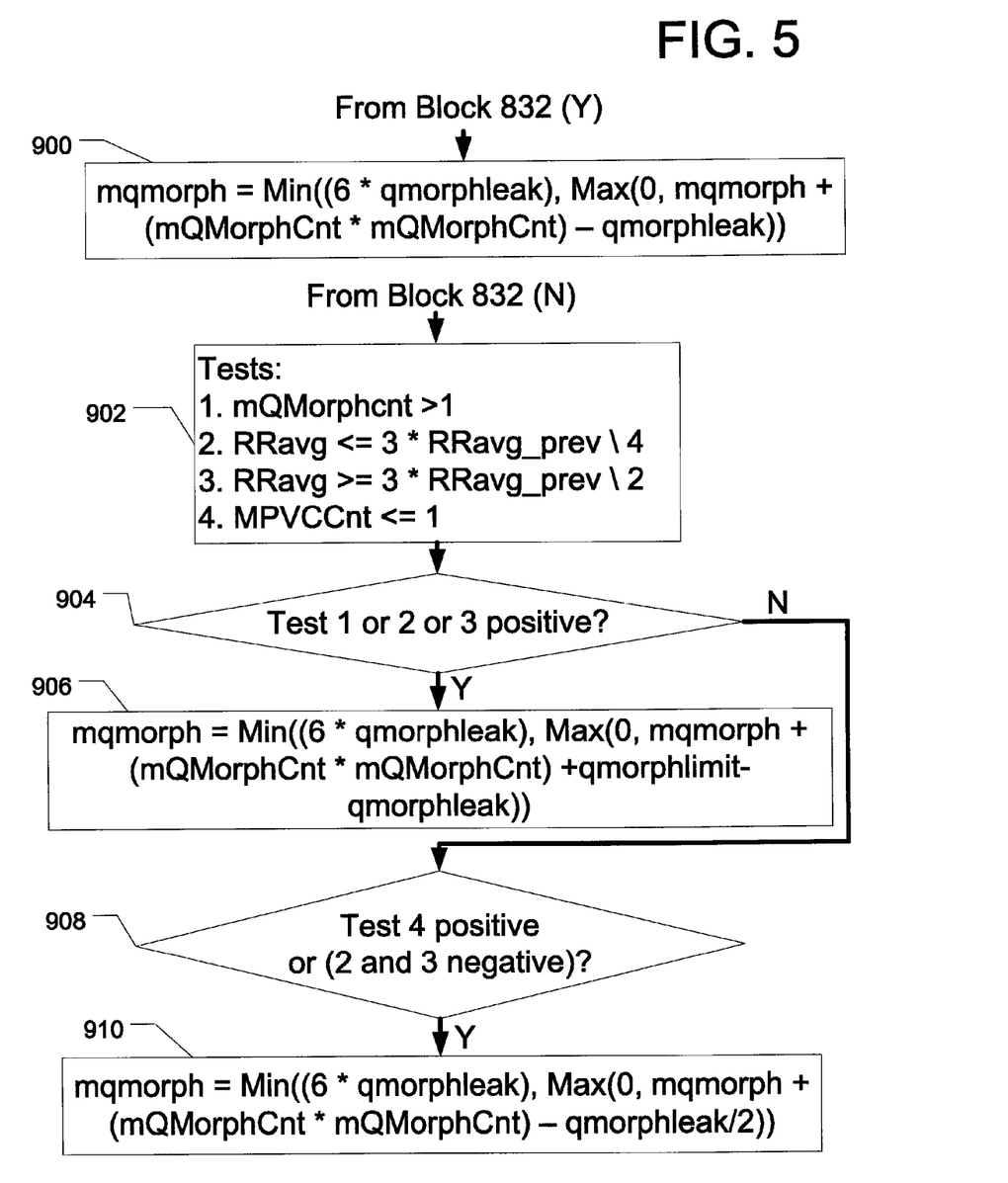
FIG. 5 is a flow chart of a routine that tracks the relative frequency of abnormal beats. Abnormal beats are determined according to QRS morphology, location of PQ and ST points, and the difference between ST deviation and long term average ST deviation. These beat based checks are performed in FIGS. 3a-3d, 4a-4b and 6.

FIG. 5 is a flow chart of a routine that tracks the relative frequency of variant beats. Variant beats are broadly defined as beats that deviate from an established pattern of normal sinus rhythm beats. Variant beats include beats that resulted in an increment of mQMoprhcnt during the QRS processing described with respect to FIG. 3a. As was described in connection with block 872 (FIG. 4b), mQMorphcnt is also updated if the average ST deviation of the segment, mStDevNavg, varies substantially from the filtered exponential average (mStDevN_xavg). Thus, sinus rhythm beats that result from an axis shift are considered variant. The relative frequency of variant beats is stored in a variable mqmorph. If mqmorph is above a threshold for a certain period of time, the system is preferably configured to respond in a user-programmable manner such as generating an alarm.

The mqmorph variable is updated after each segment is processed. The manner in which mqmoprh is updated depends on the outcome of the test applied in blocks 830 and 832 (FIG. 3d). If the outcome of this test suggests that the current segment is relatively "normal", mqmorph is computed in block 900. In particular, in block 900, mqmorph is increased by mQMorphCnt2−qmorphleak, subject to the constraints that mqmorph can not be negative or greater than 6*qmorphleak, where qmrophleak is a parameter. According to the above equation that updates mqmorph, qmorphleak acts like a "drain" that tends to "empty" mqmorph. Thus, mqmorph tends to remain at a low value unless there are a number of segments within a relatively short period of time with relatively high mQMorphCnts.

If the segment is considered relatively "abnormal" according to the test applied in blocks 830 and 832, control passes to blocks 902 and 904, which together implement another series of tests. If mQMorphcnt is greater than 1 or the segment's average RR interval is very different from the previous segment's RR interval, then mqmorph is increased in block 906 by mQMorphCnt2+qmorphlimit−qmorphleak, subject to the same constraints on the maximum and minimum mqmorph values described with respect to block 900.

Returning to block 904, if none of tests 1, 2 or 3 is positive, then control passes to block 908, which determines whether the RR interval is within ¾ and 1.5 time the previous RR interval, or the number of PVC's is low (less than 2). If so, block 910 increases mqmorph in the same manner as block 900 except that qmorphleak is divided by 2.

FIGS. 6a and 6b are collectively a flowchart that shows the preferred method for computing ST points. An analogous method may also be implemented to locate PQ points. In block 1002 of FIG. 6a, the ST search window is set between maxQRS_ind samples and maxQRS_ind+16 samples. In block 1004, the slope of the slope ("second finite difference") of the signal is computed by applying the same weighted sample averaging to the slope that was used to compute the slope itself (see discussion block 810 of FIG. 3b). The search stops at the first sample at which the second finite difference is less than a specified multiple (ST_coef) of QR_xavg, an exponential average of QR (the peak to peak QRS amplitude, as previously described). In the preferred embodiment, ST_coef is 1. If such a qualifying sample is found (at sample j), block 1006 transfers control to block 1007, which sets a new search window starting at the sample after j (sample j+1) and again ending at maxQRS_ind+16. In block 1009, this window is searched for two consecutive samples at which the absolute value of the second finite difference is less than ST_coef*QR_xavg.

If two such consecutive samples are found, with the latter of the two labeled as "k", control is transferred to block 1008 (FIG. 6b), which sets the ST point (ST_ind) based on the value of k, subject to constraints on the location of the ST point. In particular, the ST point must be at least 2 samples after the Spt (defined in block 803 of FIG. 3a), and within a 1 sample window centered on Rpeak_ind+ST_int, where ST_int is an adaptive parameter that governs the location of the ST point.

Specifically, if k is within this one sample window, then the ST point (ST_ind) is chosen as the sample k. Otherwise, if k is before this window (i.e. closer to Spt than the beginning of this window), then ST_ind is set at the earliest sample in this window, Rpeak_ind+STint−1, subject to the previously mentioned constraint regarding the location of ST_ind relative to the Spt. If k is after the window, then ST_ind is set at the latest sample in this window, Rpeak_ind+STint+1).

Block 1008 then transfers control to block 1012, which updates the adaptive parameter ST_int according to the number of samples between ST_ind and Rpeak. ST_int is preferably updated according to an exponential average filter.

Returning to block 1006, if no second finite difference within the ST point search window was less than the threshold, then control transfers to block 1010, which increments mQMorphcnt. Similarly, if no qualifying sample is found in block 1011, control is transferred to block 1010.

The routine shown in FIGS. 6a and 6b may be modified to locate PQ points. In this case, the preferred search window (block 1002) is [MinQRSInd−4, MinQRSInd−20]. ST_coef in block 1004 is −1 while the absolute value of ST_coef, 1, is used in block 1009. The sign of ST_coef will depend on expected QRS morphology; in the case of a QRS with a V2 like morphology (small R, large S), the curvature of the PQ and ST segments have opposing signs. In block 1008, the PQ point is not allowed to come within four samples of the R wave peak (i.e., maximum value of the initial upstroke of the QRS before the large downstroke.)

As is well known, integer based arithmetic, which is the preferred system for carrying out the operations described with reference to FIGS. 3-6, can produce undesirable results if the pertinent operands do not have sufficient granularity. For example, if 10 is divided by 6, the result is 1, compared to the desired result of 5/3. To reduce these types of problems, the data may be appropriate scaled. Continuing with the above example, if 10 is scaled up to 100 and then divided by 6, the result is 16, which (when divided by 10), is closer to the desired number 5/3. Appropriate scaling is performed to compare quantities that have been maintained at different scales. Continuing with the above example, if a threshold (to be applied to the value 10/6) is 2, it is scaled to 20, which may then be compared with the scaled value of 16.

For ease of understanding, the scaling factors (which are device and data dependent) have been omitted from the description of FIGS. 3-6. The preferred scaling factors for various quantities are as follows. With regard to FIGS. 4a and 4b, mStDevNavg and mStDevN_xavg are both scaled by a factor of 16. With regard to FIG. 6, ST_int and ST_ind-Rpeak_ind are scaled by a factor of 16 for purposes of computing the exponential average in block 1012. Because integer based arithmetic results in rounding down of fractions, the quantity of ½ is added to compensate for bias that would otherwise result from such truncation. For example, in block 1008 in FIG. 6b, the quantity STint+1 is computed as (16*STint+16+8)/16. All QR related quantities (used for ST deviation normalization and in block 1004 of FIG. 6a) are scaled by a factor of 128.

The invention claimed is:

1. A cardiac monitor comprising:
   (a) a sensor for sensing an analog signal from a human heart;
   (b) a device coupled to the sensor, the device having an analog-to-digital circuit system contained therein for digitizing the analog signal to produce a digitized waveform;
   (c) a processor electrically coupled to the analog-to-digital circuit system, said processor configured to:
      (i) detect a QRS complex within the digitized waveform, the QRS complex characterized by having an R wave;
      (ii) determine the location of a fiducial point within the QRS complex;
      (iii) perform a search for a point outside the QRS complex that meets a slope based criterion;
      (iv) if a qualifying point is found that meets the slope based criterion, determine a location of a non-QRS point within an adaptive window that is defined by a plurality of window parameters;
      (v) update at least one of plurality of window parameters based on the location of the non-QRS point; and
      (vi) repeat step (iv) for a different QRS complex with the adaptive window updated at least in part according to step (v).

2. The system of claim 1 wherein the non-QRS point is an ST segment point.

3. The system of claim 1 wherein the slope based criterion is based on a second finite difference of the waveform.

4. The system of claim 3 wherein the slope based criterion is based a comparison between the second finite difference and a threshold.

5. The system of claim 4 wherein the threshold is a function of QRS amplitude.

6. The system of claim 1 wherein one of the plurality of window parameters is distance from the fiducial point, and wherein this distance is updated in step (iv).

7. The system of claim 6 wherein the size of the adaptive window is fixed.

8. The system of claim 6 wherein the fiducial point is the R wave peak.

9. The system of claim 1 wherein the search for a qualifying point is performed within an initial search window.

10. The system of claim 9 wherein the initial search window begins at a point that is determined according to a location of a point in the QRS wherein the slope of the waveform is less than a certain threshold.

11. The system of claim 1 wherein the adaptive window parameter is updated according to an exponential average filter.

12. The system of claim 1 wherein the location of the non-QRS point is the end of the adaptive window if the qualifying point is after the adaptive window, and wherein the location of the non-QRS point is the beginning of the adaptive window if the qualifying point is before the adaptive window.

* * * * *